United States Patent [19]

Lueschen

[11] Patent Number: 5,049,072
[45] Date of Patent: Sep. 17, 1991

[54] O-RING ATTACHMENT SYSTEM FOR DENTAL PROSTHESIS

[75] Inventor: Jeffrey D. Lueschen, Carlsbad, Calif.

[73] Assignee: Calcitek, Inc., Carlsbad, Calif.

[21] Appl. No.: 543,656

[22] Filed: Jun. 26, 1990

[51] Int. Cl.⁵ .................. A61C 8/00; A61C 13/12; A61C 13/225
[52] U.S. Cl. .................. 433/173; 433/177
[58] Field of Search ............ 433/173, 174, 175, 176, 433/219, 177, 141

[56] References Cited

U.S. PATENT DOCUMENTS

| | | | |
|---|---|---|---|
| 2,866,285 | 3/1957 | Gerber | 433/219 |
| 3,656,236 | 4/1972 | Kurer | 433/174 |
| 4,177,562 | 12/1979 | Miller et al. | 433/174 |
| 4,193,194 | 3/1980 | Dalise | 433/177 |
| 4,204,321 | 5/1980 | Scott | 433/177 |
| 4,609,354 | 9/1986 | Koch | 433/173 |
| 4,681,542 | 7/1987 | Baum | 433/172 |
| 4,872,839 | 10/1989 | Brajnovic | 433/174 |
| 4,976,739 | 12/1990 | Duthie, Jr. | 433/174 |

Primary Examiner—John J. Wilson
Assistant Examiner—Cindy A. Cherichetti
Attorney, Agent, or Firm—John R. Merkling

[57] ABSTRACT

An o-ring attachment system with opposed convex circumferential surfaces for removable dentures to be attached to a natural or an implanted fixed root system. The o-ring attachment system can be screwed into an implanted root using a manipulating means interposed between o-ring abutment and an attachment screw. In connection therewith, a tool is provided for implanting the o-ring attachment system, the tool having a captured toroidal spring for gripping the attachment system.

20 Claims, 2 Drawing Sheets

O-RING ATTACHMENT SYSTEM FOR DENTAL PROSTHESIS

FIELD OF INVENTION

My invention relates to removable dentures attached to a natural or an implanted fixed root system. Specifically, I have invented an o-ring attachment system with opposed convex circumferential surfaces to reduce implantation stresses in an o-ring. I have also invented an o-ring attachment system which can be screwed into an implanted root using manipulating means interposed between an o-ring abutment and an attachment screw. In connection therewith, I have invented a tool for implanting the o-ring attachment system.

BACKGROUND OF THE INVENTION

Artificial teeth and dentures are frequently secured to a patient's jaw with apparatus which permits dentures to be removed. Some of these apparatus comprise o-rings for attaching a removable denture to a natural or an implanted fixed root system. Such an apparatus is disclosed, for example, in U.S. Pat. No. 4,193,194 to Dalise. An another apparatus is disclosed in U.S. Pat. No. 4,681,542 to Baum. In both of these systems an o-ring is introduced into a concave retainer cavity. The concave surfaces in the retainer cavity form a relatively sharp edge between the cavity and the rest of an o-ring abutment. Since it is contemplated that the denture may be atched and removed multiple times, excess stress and unwanted wear may be produced in the o-ring as the denture is either attached or removed.

SUMMARY OF MY INVENTION

I have invented an o-ring attachment system for dental prostheses having an o-ring abutment formed with convex surfaces. Convex abutment surfaces allow one to place an o-ring on the abutment with less potential damage to the o-ring. Because of the convex surfaces, when the o-ring is distended as it is placed on the abutment, the slope of the adjacent surface of the abutment is small relative to the direction of motion of the o-ring and the o-ring can be placed on the abutment more easily. On the other hand, when the o-ring is seated on the abutment, the adjacent surfaces have a relatively steep slope and the o-ring is securely placed on the abutment.

I have also invented an apparatus for implanting the abutment onto an implanted root or other structure. My implantation apparatus comprises manipulating means, preferably a male hexagonal section, interposed between the o-ring abutment and a screw. I have invented a seating tool having a captured toroidal spring for driving the o-ring abutment into the implanted root. The seating tool has a female hexagonal segment which is held against the male hexagonal segment when the toroidal spring engages the o-ring abutment.

It is an object of my invention, to provide an o-ring attachment system which reduces undesirable wear and stresses in an o-ring during attachment or removal of a dental prosthesis or denture.

Another object of my invention is to provide such an o-ring attachment system having convex surfaces on an o-ring abutment.

It also an object of my invention to provide an o-ring attachment system with means for manipulating the o-ring abutment, the manipulating means comprising the male hexagonal segment interposed between the o-ring abutment and a screw. It is also an object of my invention to provide an apparatus for manipulating the o-ring abutment which can be sterilized.

A further object of my invention is to provide the manipulating means having means adapted to co-operate with the seating means on the o-ring abutment and a toroidal metal spring for engaging the o-ring abutment in lieu of the elastomeric o-ring.

These and other objects of my invention will be apparent from the following description taken with reference to the accompanying drawings.

DETAILED DESCRIPTION OF THE PREFERRED EMBODIMENT

I will now describe my preferred embodiment of my invention by reference to the accompanying drawings. Like numerals designate like parts in each of the figures.

Figure 2:
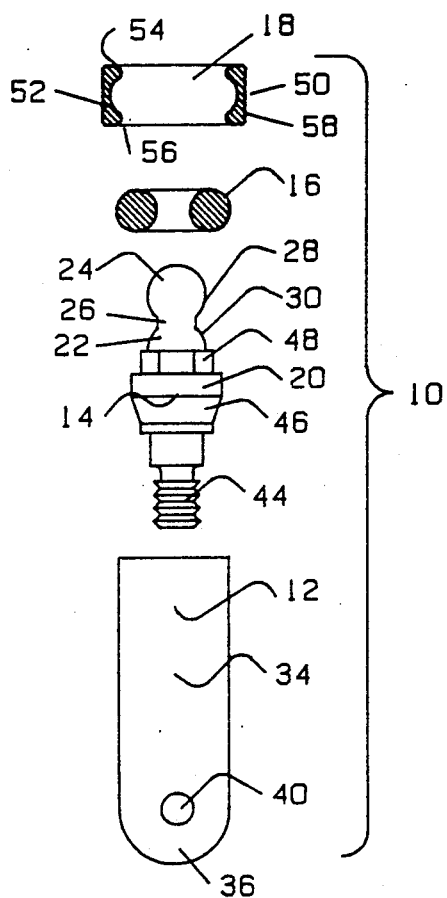
FIG. 2 is plan view and partial through-section of the o-ring attachment system taken along line 2—2 of FIG. 1.
Figure 1:
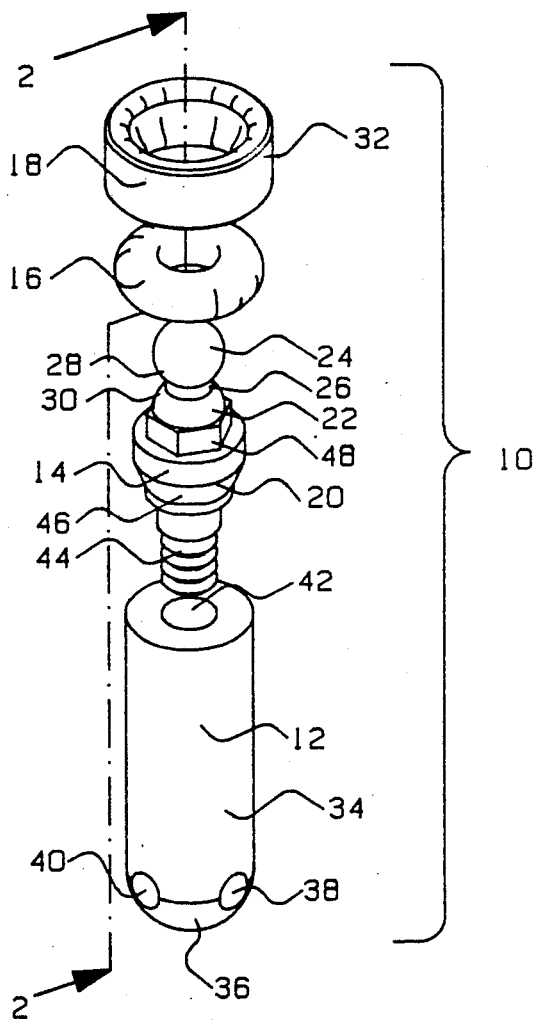
FIG. 1 is a perspective view of an o-ring attachment system according to my present invention.

FIG. 1 illustrates an o-ring attachment system, generally designated 10, according to my present invention. The attachment system comprises an implanted root 12, an o-ring abutment or post 14, an elastomeric o-ring 16, and a retainer 18. The root 12 can be securely implanted in a mandible of a patient, as is known in the art. After implantation of the root, a period for healing and incorporation of the root into the mandible structure may be needed. Thereafter, the o-ring abutment 14 can be attached to the root. I prefer to use a threaded screw 20, but other attachment mechanisms are known and can be employed in connection with my invention. In my invention, the o-ring abutment comprises a hemispherical base 22 and a spherical end 24 separated by a cylindrical spacer 26. The spherical end 24 and the hemispherical base 22 form opposing convex surfaces 28, 30, respectively, adapted to retain the elastomeric o-ring 16. The retainer 18 fits over the o-ring 16 and provides an attachment surface 32 which can be connected to a dental prosthesis or denture, as is known in the art.

The convex surfaces on the on-ring abutment or post permit one to place the o-ring on the o-ring abutment without excessive stress or wear in the o-ring. The o-ring can also be removed from the abutment in a similar fashion. As the o-ring 16 passes over the spherical end 24 it will be stretched. As the distention of the o-ring increases, the slope of the surface of the spherical end adjacent the o-ring decreases with reference to the direction of motion of the o-ring. The rate of distention of the o-ring is, consequently, relatively reduced and there are no abrupt changes in stress or relatively sharp edges which might damage the o-ring, reducing its structural integrity. When the o-ring is seated on the o-ring abutment and adjacent the cylindrical spacer, the surfaces of the spherical end and the hemispherical base present relatively steep angles to axial motion of the o-ring.

Consequently, the o-ring attachment system can secure the dental prosthesis from undesirable removal.

In my preferred embodiment, the implanted root 12 comprises a cylinder 34 having a hemispherical tip 36. As is known in the art, attachment of the root 12 to the bone of the mandible can be promoted by a coating of hydroxyapatite. Through bores 38, 40 can be provided for additional bony ingrowth. A threaded bore 42 is provided to receive the threaded screw 20 of the o-ring abutment.

The threaded screw 20, comprises a threaded shank 44 and a tapered seat 46 so that the abutment 14 can be tightly attached or screwed into the root 12. Between the hemispherical base 22 and the tapered seat 46, I have placed a male hexagonal section 48 for screwing the abutment into the root. A seating tool, which I will describe hereafter, grips the o-ring abutment and engages the male hexagonal section.

After the o-ring abutment is attached to the root, the o-ring 16 can be placed on the abutment. Alternatively, the o-ring may be placed in the retainer 18 which should already be encased within the denture or dental prosthesis and the assembly of the denture, retainer and o-ring can be placed on the abutment as a single unit.

In my referred embodiment, the retainer 18 comprises a ring 50 with a concave grove 52 on the inside thereof. Interior upper and lower edges 54, 56 respectively, should be rounded to minimize or prevent damage to the o-ring. An outer surface 58 of the retainer may be textured to enhance mechanical coupling between the denture and the retainer.

Figure 3:
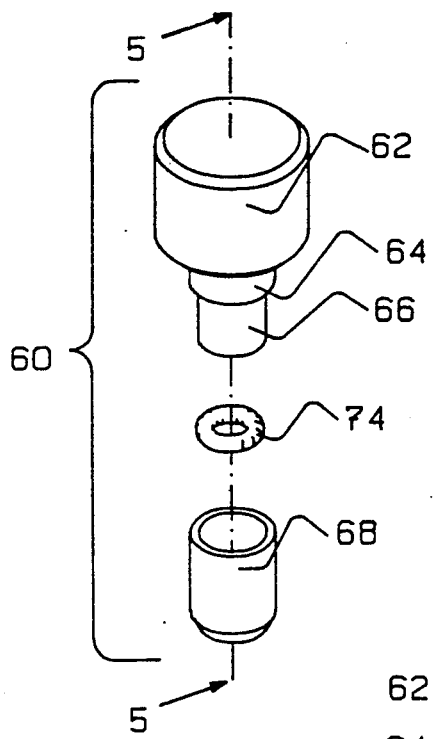
FIG. 3 is a perspective view of a seating tool for use with the attachment system of FIG. 1.
Figure 5:
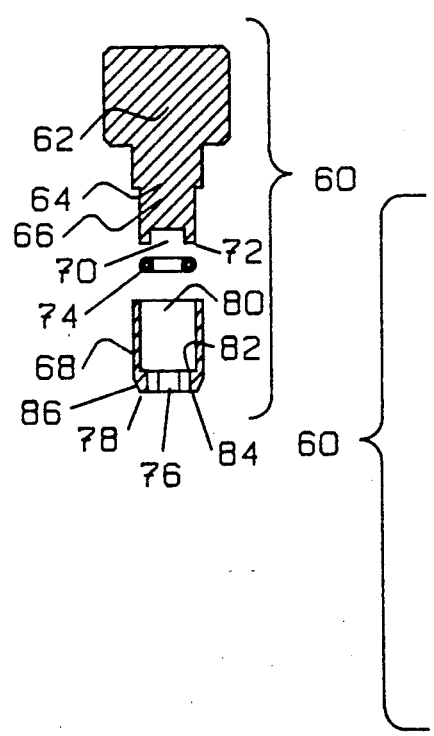
FIG. 5 is a through-section of the seating tool taken along line 5—5 of FIG. 3.
Figure 4:
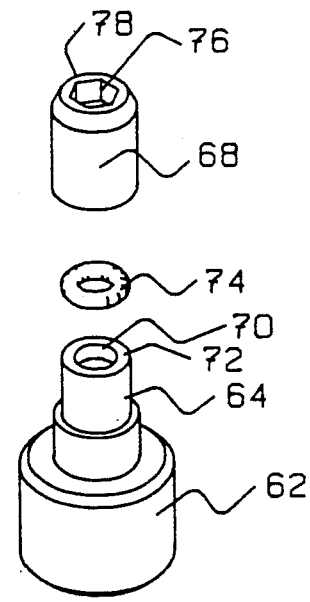
FIG. 4 is an inverted perspective view of the tool of FIG. 3.

To install the o-ring abutment 14 on the implanted root 12, I have invented a seating tool 60 shown in exploded perspective view in FIG. 3. The seating tool 60 comprises a knurled handle 62 with a shaft 64. A distal end 66 of the shaft 64 has a smaller diameter to receive a sleeve 68. As can be seen in FIG. 4, there is a counter bore 70 in a distal end 72 of the shaft 64. A toroidal coil spring 74 is placed against the distal end 72 of the shaft. The toroidal spring acts like the elastomeric o-ring and can grip the o-ring abutment near the cylindrical spacer 26 to hold the o-ring abutment in the seating tool 60. Because the toroidal spring is metal, the tool can be sterilized in an autoclave. Moreover, the spring does not tend to weaken or degrade as an elastomeric o-ring might under repeated use.

With the spring 74 in place, the sleeve 68 is placed over the spring and press fit onto the shaft 64. The sleeve 68 has a hexagonal female bore 76 at a distal end 78 thereof. The hexagonal bore 76 is adapted to engage the male hexagonal section 48 on the o-ring abutment, so that the o-ring abutment can be screwed into the root 12. The sleeve 68 defines a partial bore 80 which encloses the spring 74 and into which the shaft 66 is pressed. This bore 80 should be slightly larger in diameter than the largest dimension of the hex bore 76 so that a lip 82 is formed which retains the spring 74 inside the sleeve 68. A distal end 84 of the sleeve is chamfered 86.

My invention may be embodied in other specific forms without departing from the spirit or essential characteristics thereof. The present embodiment is considered in all respects to be illustrative and not restrictive, the scope of my invention being indicated by the appended claims, rather than the foregoing description and all changes which come within the meaning and range of equivalency of the claims are therefore intended to be embraced therein.

I claim as my invention:

1. A removable denture attachment system for use with a natural or implanted fixed root system which comprises in combination:
    an elastomeric ring;
    a post;
    means for securing the post to the natural or implanted root in the patient's mouth;
    said post further comprising a hemispherical base proximal of the securing means and a spherical end distal from the securing means, said hemispherical base and said spherical end forming opposed convex circumferential walls for receiving the elastomeric ring;
    an annular retainer surrounding the elastomeric ring;
    a denture surrounding said annular retainer, said ring and said post; and
    means for manipulating the post securing means, the manipulating means comprising a faceted segment interposed between the hemispherical base and the securing means.

2. The removable denture attachment system according to claim 1 wherein the post further comprises a spacer between the spherical end and the hemispherical base.

3. The removable denture attachment system according to claim 2 wherein the spacer is a cylinder.

4. The removable denture attachment system according to claim 1 further comprising means for engaging the manipulating means.

5. A removable denture attachment system for use with a natural or implanted fixed root system which comprises in combination:
    an elastomeric ring;
    a post;
    means for securing the post to the natural or implanted root in the patient's mouth;
    said post further comprising a hemispherical base proximal to the securing means and a spherical end distal from the securing means, said hemispherical base and said spherical end forming opposed convex circumferential walls for receiving the elastomeric ring;
    an annular retainer surrounding the elastomeric ring;
    a denture surrounding said annular retainer, said ring and said post;
    means for manipulating the post securing means, the manipulating means comprising a faceted segment interposed between the hemispherical base and the securing means; and
    means for engaging the manipulating means, said manipulating means engaging means comprising means for gripping the opposed convex circumferential walls.

6. The removable denture attachment system according to claim 5 wherein the gripping means comprise a toroidal spring.

7. The removable denture attachment system according to claim 6 wherein the securing means comprise a screw.

8. The removable denture attachment system according to claim 5 wherein the faceted segment comprises an hexagonal male segment.

9. The removable denture attachment system according to claim 8 further comprising means for engaging the manipulating means.

10. The removable denture attachment system according to claim 9 wherein the manipulating means engaging means comprise means for gripping the opposed convex circumferential walls.

11. The removable denture attachment system according to claim 10 wherein the gripping means comprise a toroidal spring.

12. The removable denture attachment system according to claim 11 wherein the securing means comprise a screw.

13. A removable denture attachment system for use with a natural or implanted fixed root system which comprises in combination:
   an elastomeric ring;
   a post, said post comprising means for receiving the elastomeric ring;
   means for securing the post to the natural or implanted root in a patient's mouth;
   an annular retainer surrounding the elastomeric ring;
   a denture surrounding said annular retainer, said ring and said post;
   means for manipulating the post and the post securing means; and
   removable means for engaging the manipulating means, said removable engaging means comprising toroidal spring means for gripping the ring receiving means.

14. The removable denture attachment system according to claim 13 wherein the ring receiving means comprise opposed convex circumferential walls.

15. The removable denture attachment system according to claim 14 wherein the post further comprises
   a hemispherical base proximal to the securing means and
   a spherical end distal from the securing means.

16. The removable denture attachment system according to claim 15 wherein the post further comprises a spacer between the spherical end and the hemispherical base.

17. The removable denture attachment system according to claim 16 wherein the spacer is a cylinder.

18. The removable denture attachment system according to claim 13 wherein the manipulating means comprise a faceted male segment interposed between the post and the securing means and wherein the removable engaging means comprise a faceted female segment adapted to engage the faceted male segment.

19. The removable denture attachment system according to claim 18 wherein the faceted male segment comprises an hexagonal male segment and wherein the faceted female segment comprises a hexagonal female segment.

20. The removable denture attachment system according to claim 19 wherein the securing means comprise a screw.

* * * * *